United States Patent [19]

Niswonger et al.

[11] Patent Number: 4,782,172

[45] Date of Patent: Nov. 1, 1988

[54] REMOVAL OF POLYFUNCTIONAL SILANES FROM ORGANOSILANES

[75] Inventors: David S. Niswonger, Louisville, Ky.; Roland L. Halm, Madison, Ind.

[73] Assignee: Dow Corning Corporation, Midland, Mich.

[21] Appl. No.: 137,893

[22] Filed: Dec. 28, 1987

[51] Int. Cl.$^4$ .............................. C07F 7/08; C07F 7/18
[52] U.S. Cl. .................................... 556/466; 556/462
[58] Field of Search ................................ 556/466, 462

[56] References Cited

U.S. PATENT DOCUMENTS

| | | | |
|---|---|---|---|
| 2,421,653 | 6/1947 | Sauer | 260/607 |
| 2,594,946 | 4/1952 | Lucas | 260/448.2 |
| 2,738,359 | 3/1956 | Hyde | 260/448.2 |
| 2,881,199 | 4/1959 | Bailey et al. | 556/462 X |
| 2,902,507 | 9/1959 | Hyde et al. | 556/466 X |
| 3,065,252 | 11/1962 | Brown et al. | 260/448.2 |
| 3,101,361 | 8/1963 | Brown et al. | 260/448.2 |
| 3,549,680 | 12/1970 | Wegehaupt et al. | 260/448.2 |
| 3,642,851 | 2/1972 | Bennett | 260/448.2 |
| 3,646,088 | 2/1972 | Bakassian | 260/448.2 |
| 3,686,253 | 8/1972 | Bennett | 260/448.2 R |
| 4,073,801 | 2/1978 | Moretto et al. | 260/448.2 E |
| 4,113,760 | 9/1978 | Frey et al. | 260/448.2 E |
| 4,176,128 | 11/1979 | Deubzer et al. | 556/462 X |
| 4,421,926 | 12/1983 | Tolentino | 556/471 |

FOREIGN PATENT DOCUMENTS

| | | | |
|---|---|---|---|
| 1087601 | 1/1960 | Fed. Rep. of Germany | 556/466 X |
| 61-254594 | 12/1986 | Japan | 556/466 X |
| 1096476 | 12/1967 | United Kingdom | 556/466 X |

Primary Examiner—Paul F. Shaver
Attorney, Agent, or Firm—Carl A. Yorimoto

[57] ABSTRACT

What is described is a process for the treatment of organosilanes to reduce the content of more highly functional silanes. The process comprises (A) contacting a mixture, the mixture comprising a major portion of the organosilane and a minor portion of the more highly functional silanes, with organosiloxanes, and a sufficient amount of a catalyst effective in promoting the reaction between the more highly functional silanes and the organosiloxane to form more highly halogenated polyfunctional siloxanes; and (B) isolating the organosilane from the polyfunctional siloxanes and the organosiloxanes by conventional means such as distillation.

22 Claims, No Drawings

REMOVAL OF POLYFUNCTIONAL SILANES FROM ORGANOSILANES

BACKGROUND OF THE INVENTION

This invention relates to a process for the conversion of more highly functional silane impurities in organosilanes to organosiloxanes to facilitate isolation and removal of these impurities from desired product organosilanes.

High-purity organosilane monomers, particularly diorganodihalosilanes, are needed for the ever-increasing quality needs for the preparation of linear organopolysiloxanes utilized in the manufacture of silicone fluids and elastomers. As an example, the preparation of high-quality, high-performance silicone elastomers require that the linear organopolysiloxanes contain a minimum level of trifunctional and tetrafunctional branching units, preferably to levels of 100 part per million (on a weight basis) or less.

For the purposes of the instant invention, the following definitions may prove helpful in understanding. "Functionality" is a definition for the ability of siloxane species to form an end-blocking structure ("monofunctionality"), a linear structure ("difunctionality"), a branched structure ("trifunctionality"), or a network structure ("tetrafunctionality").

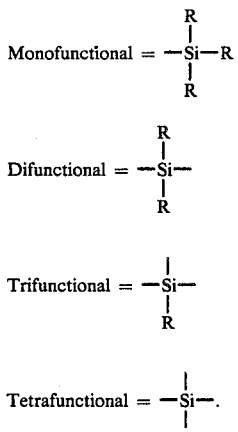

"More highly functional silane" means that a tetrafunctional silane is more highly functional than a trifunctional silane, that a trifunctional silane is more highly functional than a difunctional silane, and so on. In the preparation of high-performance silicone elastomers, as an example, difunctional siloxane monomers with a minimum of more highly functional trifunctional and tetrafunctional branching units are a necessity. A mixture of dimethyldichlorosilane and a minor amount of methyltrichlorosilane is an example of a difunctional material that contains a trifunctional impurity.

In the manufacture of organosilanes, separation of the individual species from the reaction mixture is conventionally effected by distillation. In many instances the boiling points of individual organosilane components are very close, creating a very difficult distillation operation. One of the more difficult distillation separations is a combination of a diorganodihalosilane and an organotrihalosilane. Examples of such combinations are the following mixtures:
dimethydichlorosilane/methyltrichlorosilane,
methylvinyldichlorosilane/vinyltrichlorosilane,
phenylmethyldichlorosilane/phenyltrichlorosilane, and
diphenyldichlorosilane/phenyltrichlorosilane.

As an example of the difficulty of separation, the boiling points of dimethyldichlorosilane and methyltrichlorosilane are approximately 4° C. apart. Reducing the methyltrichlorosilane content of dimethyldichlorosilane to levels sufficient for the quality requirements of the silicone industry presently requires extensive distillation. Present distillation requires large capital outlays for distillation equipment and high energy consumption in the form of steam to generate the large reflux requirements needed to accomplish this difficult separation. To illustrate this point, Lucas in U.S. Pat. No. 2,594,946, issued Apr. 29, 1952, discloses that when one fractionally distills the dimethyldichlorosilane obtained from the direct process reaction of silicon with methyl chloride, even the most careful fractionation through a 200-plate column gives dimethyldichlorosilane which contains approximately 99.6 mole percent dimethyldichlorosilane and 0.4 mole percent methyltrichlorosilane.

Sauer, U.S. Pat. No. 2,421,653, issued June 3, 1947 discloses that halogensilanes and organopolysiloxanes undergo equilibration to form mixtures comprising some unreacted halogensilanes and organosiloxanes plus a mixture of polyorganohalogenosiloxanes. Brown and Hyde, U.S. Pat. No. 3,065,252, issued Nov. 20, 1962, discloses the interaction of halosilicon compounds with organosiloxanes in the presence of certain catalysts. The catalysts disclosed by Brown and Hyde are aminoalkyl-substituted organosilicon compounds and their salts with hydrogen halides, salts of monocarboxylic acids, aliphatic amines and hydrogen halide salts, and quaternary ammonium halides. Brown and Hyde, U.S. Pat. No. 3,101,361, issued Aug. 20, 1963, discloses the use of inert polar solvent such as halogenated hydrocarbons, nitriles, nitrohydrocarbons, and amides in the interaction of halosilanes and organopolysiloxanes. Wegehaput et al., U.S. Pat. No. 3,549,680, issued Dec. 22, 1970, discloses the use of certain phophorous-nitrogen compounds as catalysts in the reaction of halosilane compounds with organosiloxanes free of halogen to produce organohalosilane compounds differing from the starting materials. Bennett, U.S. Pat. No. 3,642,851, issued Feb. 15, 1972; and Bennett, U.S. Pat. No. 3,686,253, issued Aug. 22, 1972, disclose the redistribution of halosilanes with cyclotrisiloxane or cyclotetrasiloxane in the presence of a phosphine oxide or amine oxide catalyst. Bakassian et al., U.S. Pat. No. 3,646,088, issued Feb. 9, 1972, discloses the distribution between a siloxane and a chlorosilane carried out in hexaalkylphosphotriamide. Moretto et al., U.S. Pat. No. 4,073,801, issued Feb. 14, 1978, discloses a process in which a chlorosilane or partial hydrolysis product is reacted with a siloxane in the presence of an equilibration catalyst and hydrogen chloride to produce a stable polymeric product of comparatively high molecular weight or high chlorine content. Nowhere in the above references is there a suggestion or demonstration of the conversion of a more highly functional silanes to halopolyorganosiloxanes as part of a process to isolate and recover an organosilane of enhanced quality.

Volker et al., U.S. Pat. No. 4,113,760, issued Sept. 12, 1978, discloses an improved process for converting organosiloxane polymers to organohalosilanes which comprises reacting halosilanes with organopolysiloxanes in the presence of activated charcoal, and if desired an inorganic acid. Volker et al., also discloses that the process can also be used as a method for purifying silanes, especially silanes containing SiH which are contaminated with organic compounds. The silanes are hydrolyzed, distilled, and once more converted into silanes. Nowhere does Volker et al., disclose or suggest the conversion of the more highly functional impurity to a polyorganosiloxane while maintaining, isolating, and recovering a organosilane, unchanged.

Lucas, U.S. Pat. No. 2,594,946, issued Apr. 29, 1952, describes the recovery of essentially pure diorganodihalosilane from a mixture of diorganodihalosilane with organotrihalosilane. Recovery is effected by treating of said mixture with a diorganodiacyloxysilane.

Hyde, U.S. Pat. No. 2,738,359, issued Mar. 13, 1956, describes a chemical method for separating silicon tetrachloride and monoorganotrichlorosilanes from dichloro and monochloroorganosilanes. Separation is effected by the selective formation of crystalline non-volatile complexes of certain amides with silicon tetrachloride and alkyltrichlorosilanes. These crystalline complexes are insoluble in diorgano and triorganochlorosilanes. Similarly, British Pat. No. 1,096,476, published Dec. 29, 1967, describes a process for the separation of an organotrichlorosilane from a liquid mixture by contacting said mixture with tris(dimethylamino)phosphine oxide and separating the solid complex formed between the organotrichlorosilane and the phosphine.

Cahoy in German Pat. No. DE 1,087,601, issued Feb. 16, 1961, describes a process in which silicon tetrachloride and methyltrichlorosilane are selectively hydrolyzed from a mixture including trimethylchlorosilane as a major portion. Selective hydrolysis is effected by using water-dioxane mixtures. It has also been found that other water-miscible solvents such as polyethylene glycols and cresol are effective in the selective hydrolysis of trifunctional chlorosilane impurities from diphenyldichlorosilanes.

Japanese Patent Publication, No. 61-254594, published Nov. 12, 1986, discloses the purification of a mixture of organosilicon compounds by adding aprotic polar solvents and alkylene oxide compounds to react selectively with the most highly chlorinated organosilicon compound and distilling the resulting mixture to recover the less chlorinated organosilcon compound.

Tolentino, U.S. Pat. No. 4,421,926, issued Dec. 20, 1983, discloses the co-alkoxylation of halosilanes to facilitate separation of close-boiling halosilane materials, difficult to separate by conventional distillation, to facilitate separation of the corresponding alkoxysilanes, having greater boiling point differences. Tolentino discloses that all halosilanes will be converted to alkoxysilane.

SUMMARY OF THE INVENTION

It is an objective of the instant invention to provide a process for significantly reducing the more highly functional silane content of organosilanes that is less costly than the present practice of purification by distillation. It is a another objective of the instant invention to convert the more highly functional silanes while not changing the desired organosilane products. Finally, it is an objective to minimize the handling and disposal of reagents and catalysts that may be required for the chemical conversion and isolation of organotrihalosilane materials.

It has been found that an organosilane containing a minor portion of an organotrihalosilane or tetrafunctional silane can be contacted with a polydiorganosiloxane to incorporate the more highly functional silane into the siloxane material to facilitate greater ease in separation of the more highly functional silane impurity from the desired organosilane. The reaction of the more highly functional silane with the polyorganosiloxane is facilitated by the presence of a catalyst such as phosphorous-containing compounds nitrogen- containing compounds, and activated carbon. The catalyst can be such a readily available, inexpensive material as phosphoric acid or activated carbon. Additionally, the polyorganosiloxane can be the corresponding siloxane of a desired diorganodihalosilane. Thus, the polyorganosiloxane is available from the subsequent processing of a diorganodihalosilane or by simple hydrolysis of a small portion of the diorganodihalosilane. The instant invention has the capability to reduce the more highly functional silane content of organosilanes down to levels of 100 parts per million or lower.

The instant invention does not require special reagents such as the diorganodiacyloxysilane as disclosed by Lucas, U.S. Pat. No. 2,594,946, the dioxane as disclosed by Cahoy, German Patent No. DE 1,087,601, or the aprotic polar solvents and alkylene oxide compounds of Japanese Patent Publication No. J 61-254594, all cited supra. Additionally, the instant invention does not require specialized and costly reagents to form solid complexes with the polyfunctional silanes as disclosed by Hyde, U.S. Pat. No. 2,738,359, and the British Patent 1,096,476, cited supra. Finally, the organosilane is recovered intact and not chemically converted to another species, such as the alkoxysilanes disclosed by Tolentino, U.S. Pat. No. 4,421,926, supra.

DESCRIPTION OF THE INVENTION

In accordance with the instant invention, there is provided a process for the treatment of an organosilane to reduce the content of more highly functional silanes under conditions that will be delineated herein. A process is described for the purification of an organosilane, having the formula, $$R^i_a SiX_{4-a},$$

wherein each $R^i$ is independently selected from a group consisting of hydrogen atoms, alkyl groups, substituted alkyl groups, alkenyl groups, and aryl groups; wherein each X is an independently selected halogen atom; wherein a has a value of 1, 2, 3, or 4; and wherein at least one $R^i$ must be an alkyl group, a substituted alkyl group, an alkenyl group, or an aryl group, wherein the content of more highly functional silanes having the formula, $$R^{ii}_b SiX_{4-b},$$

wherein each $R^{ii}$ is independently selected from a group consisting of alkyl groups, substituted alkyl groups, alkenyl groups, aryl groups, and substituted aryl groups; wherein b has a value of 0, 1, 2, or 3 and b must be less than a: and wherein X is defined above, is reduced, said process comprising
(A) contacting a mixture comprising a major portion of the organosilane and a minor portion of one or more more highly functional silane, with organosiloxanes, and a sufficient quantity of a catalyst effective in promoting reaction between said more highly functional silanes and said organosiloxanes, wherein the organosiloxanes are selected from a group consisting of

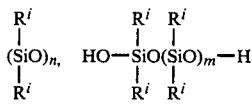

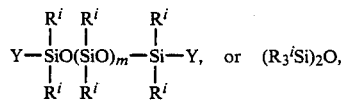

wherein $R^i$ is defined above; wherein each Y is independently selected from a group consisting of halogen atoms and trialkylsiloxy groups; wherein n has a value of 3 to 9, inclusive; and wherein m has a value of less than about 1000;

(B) facilitating the reaction between the more highly functional silanes and the organosiloxane to convert the more highly functional silanes to polyfunctional siloxanes, said polyfunctional siloxanes having the formula,

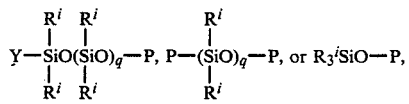

wherein each P is independently selected from a group consisting of $-SiR^{ii}_2X$, $-SiR^{ii}X_2$, and $-SiX_3$ radicals, wherein each $R^{ii}$, X, and Y are independently selected and are defined above; and wherein q has a value of less than about 1000; and (C) isolating the organosilane from the more highly functional siloxanes and the organosiloxanes.

The process described can be more specifically applied to purification of an organosilane having formula, $R^i_c SiX_{4-c}$, wherein $R^i$ and X are defined above, and c has a value of 2, 3, or 4. Further, the more highly functional silane can have the formula, $R^{ii}_d SiX_{4-31\ b}$, wherein $R^{ii}$ and X are defined above, and d has a value of 0 or 1.

The process can further comprise in (B) contacting a hydrogen halide with said mixture of organosilane and more highly functional silanes, said organosiloxanes, and said catalyst. The hydrogen halide is believed to yield a beneficial effect upon the conversion of the more highly functional silanes to polyfunctional siloxanes. The hydrogen halide can be, for example, hydrogen fluoride, hydrogen chloride, hydrogen bromide, or hydrogen iodide.

For the purposes of the instant invention, in describing the catalyst, the term "effective in promoting the reaction between the more highly functional silanes and the organosiloxanes" refers to any catalyst which promotes the reaction of the more highly functional silanes with the organosiloxanes to form polyfunctional siloxanes. Examples of such catalysts include phosphorous-containing compounds, nitrogen-containing compounds, and activated carbon. The phosphorous-containing compounds can be, for example, phosphoric acids, organophosphoric acids, organophosphonates, phosphonitrile halides, quaternary phosphonium halides, and phosphine oxides. The nitrogen-containing compounds can be, for example, aliphatic amines, aromatic amines, quaternary ammonium hydroxides, quaternary ammonium halides, amine hydrohalides, carboxylic acid salts of amines, and carboxylic acid salts of quaternary ammonium hydroxides. The catalysts may also be on a solid support. The solid support may be, for example, an organic resin, silica gel, or activated carbon. The preferred catalysts are phosphoric acid and activated carbon.

The phosphorous-containing compounds should be present at a concentration of greater than about 0.1 weight percent relative to the mixture of the organosilane and the more highly functional silane. Concentrations of the phosphorous-containing compounds lower that 0.1 weight percent are believed to promote the reaction. However, these lower concentrations could require longer contact times and could be more susceptible to deactivation and poisoning. The preferred concentration of the phosphorous-containing compounds is in a range from about 0.1 to 10 weight percent. Higher concentrations of the phosphorous-containing compound could be utilized; however, no additional benefit is perceived.

The above description is believed by the inventors to be applicable to nitrogen-containing compounds.

The concentration of activated carbon as a catalyst relative to the mixture of organosilane and the more highly functional silane should be greater than about 2.0 weight percent.

Non-branching organosilane monomers which are purified include, for example, methyltrifluorosilane, methyltrichlorosilane, ethyltribromosilane, ethytrichlorosilane, i-propyltrichlorosilane, n-butyltrichlorosilane, phenyltrichlorosilane, vinyltrichlorosilane, allyltribromosilane, trifluoropropyltrichlorosilane, dimethyldichlorosilane, dimethyldibromosilane, methyldichlorosilane, methylethyldichlorosilane, diethyldichlorosilane, phenylmethyldichlorosilane, diphenyldichlorosilane, phenyldichlorosilane, methylvinyldichlorosilane, ethylallyldibromosilane, trifluoropropylmethyldichlorosilane, trimethylchlorosilane, dimethylchlorosilane, t-butyldimethylchlorosilane, diphenylmethylchlorosilane, dimethylvinylchlorosilane, methylphenylvinylchlorosilane, tetramethylsilane, or tetraethylsilane.

The more highly functional silane monomers which are removed in this process include, for example, any of the above organosilane monomers, except the tetraorganosilanes. Further, the more highly functional silane monomers can include, for example, tetrafluorosilane, tetrachlorosilane, tetrabromosilane, tetraiodosilane, or substituted alkyl and substituted aryl silanes such as, $Cl_3SiC_6H_{10}SiCl_3$, $Cl_2C_6H_5SiCH_2SiCl_3$, $(SiCl_3)_2C_6H_3SiCl_3$, $(SiCl_3OSiCl_2)C_6H_4SiCl_3$, $C_6H_5SiCl_2CH(CH_3)SiCl_3$, $C_5H_{11}C_6H_4SiCl_3$, $Cl_3SiC_6H_4CH_2SiCl_3$, or $C_3H_7SiCl_2C_6H_4SiCl_3$. The initial concentration of the polyfunctional silane in organosilane will normally be greater than about 0.1 weight percent. The initial concentration of the polyfunctional silane will generally be in the range of from about 0.1 to 5.0 weight percent.

Organosilanes are produced as mixtures from the various commercial processes. As an example, in the preparation of methylchlorosilanes from the direct reaction of silicon with methyl chloride, the major product is dimethyldichlorosilane with various combinations of methyl, chloro, and hydrogen-containing silanes as minor products. The various methylchlorosilanes are separated and isolated by conventional means such as distillation. However, isolation of dimethyldichlorosilane from methyltrichlorosilane contamination becomes very difficult by conventional distillation at concentrations lower than about 1 weight percent. Conventional distillation readily reduces the methyltrichlorosilane content of dimethyldichlorosilane to levels in a range of from about 0.5 to 2.0 weight percent. Levels of methyltrichlorosilane down to about 0.1 weight percent and lower are achieved through very extensive distillation, large numbers of distillation stages and very high reflux back to the distillation column.

The organosiloxanes which can be used to combine with the more highly functional silane includes cyclopolydiorganosiloxanes, hydroxy-endblocked linear polydiorganosiloxanes, halo-endblocked linear polydiorganosiloxanes, trialkylsiloxy- endblocked linear polydiorganosiloxanes, or hexaorganodisiloxanes. Examples of cyclopolydiorganosiloxanes are hexamethylcyclotrisiloxane, octamethylcyclotetrasiloxane, tetramethyltetravinylcyclotetrasiloxane, or hexaphenylcyclotrisiloxane. Examples of linear polydiorganosiloxanes are

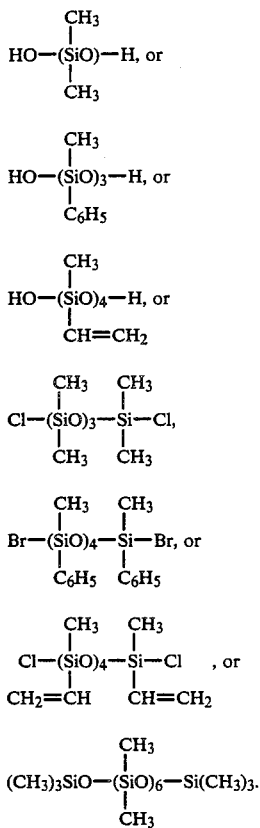

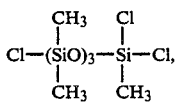

The hexaorganodisiloxane can be, for example, hexamethyldisiloxane, tetramethyldivinyldisiloxane, or dimethyldiphenyldivinyldisiloxane.

Depending upon the organosiloxane used and the more highly functional silane to be removed, a corresponding more highly functional siloxane will be formed. The polyfunctional siloxanes may be, for example,

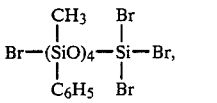

-continued

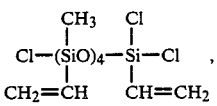

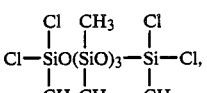

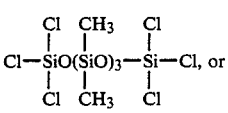

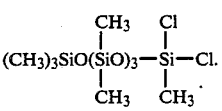

$$(CH_3)_3SiO(\overset{\overset{\displaystyle CH_3}{|}}{\underset{\underset{\displaystyle CH_3}{|}}{Si}}O)_3-\overset{\overset{\displaystyle Cl}{|}}{\underset{\underset{\displaystyle CH_3}{|}}{Si}}-Cl.$$

The organosiloxanes should be present at a concentration of greater than about 1 weight percent relative to the mixture of the organosilane and the more highly functional silane. A chemical equilibrium is established among the organosilane, the more highly functional silane, the organosiloxanes and the polyfunctional siloxanes. An organosiloxane concentration of 1 weight percent is believed to be a lower limit at which the more highly functional silanes are effectively converted to polyfunctional siloxanes. Lower concentrations of organosiloxanes may be utilized; however, the conversion of the more highly functional silanes will be reduced. Organosiloxane concentrations of 10 to 20 weight percent are preferred. However, higher concentrations of organosiloxanes may be utilized without any detrimental effect. To minimize the loss of value of the organosiloxane, the mixture of organosiloxanes and polyfunctional siloxanes may be recycled. However, recycle will be limited by the chemical equilibrium, discussed supra, and the needed level of more highly functional silanes in the purified organosilane.

The reaction of the more highly functional silane with organosiloxanes has been found to proceed at ambient temperature, or temperatures greater than about 20° C. Higher temperatures are beneficial in improving reaction rate. However, it is believed that temperatures of greater than about 200° C. may be detrimental to product quality by creating cleavage of organic groups and creating additional more highly functional silanes.

Reaction among the mixture of the organosilane and the more highly functional silane, the organosiloxanes, and the catalyst can occur very rapidly given proper catalyst and temperature conditions. The reaction can be completed in a matter of a few minutes or less.

Once the more highly functional silanes are converted to polyfunctional siloxanes, the higher boiling point of the polyfunctional siloxanes as compared to the desired organosilane facilitates isolation of the organosilane with a significantly reduced content of more highly functional by conventional distillation. The distillation requirements can be several orders of magnitude less than needed for the separation of more highly functional silanes from the desired organosilane, absent the instant invention.

Applying the instant invention, reduction of the more highly functional silane content of the organosilanes of greater than 80% can be realized. As an example, for the separation of methyltrichlorosilane from dimethyldichlorosilane reductions of methyltrichlorosilane content of greater than 90% and more typically 99% or more can be realized.

The process of the instant invention can be carried out in a batch mode. The batch mode can be, for example, a conventional batch reactor with provision for mixing, such as a mechanical agitator to facilitate contact of the reactants and catalyst. The batch reactor can also have provisions for heating and cooling, as well as provisions for operation under pressure to assure that the reactor contents remain in a liquid phase. The batch reactor can also be integrated to a conventional batch or continuous distillation column.

The process of the instant invention can also be carried out in a continuous mode. The continuous mode can be, for example, a column type reactor, such as a conventional packed column or a tray column. The continuous reactor can be fitted with separate or combined feed systems for the halosilane, siloxane, and catalyst feeds. These feed systems can be conventional pumps with appropriate means for flow control. The continuous reactor can be provided with means for heating, cooling, and operation under pressure. A continuous reactor system can also have distillation integral to the system to continuously recover the purified organosilane. Alternately, the distillation can be separate from the reactor system.

So that those skilled in the art may better appreciate and understand the instant invention, the following examples are presented. These examples are presented to be illustrative and are not to be construed aslimiting the claims as delineated herein.

EXAMPLE 1

(Not within the scope of the instant invention).

Approximately 100 g of a mixture consisting of about 1% by weight methyltrichlorosilane (Me), 94% dimethyldichlorosilane ($Me_2$), and 5% octamethylcyclotetrasiloxane ($D_4$) were added to a laboratory reactor fitted with an agitator and provisions for heating and venting of gases. To the agitated silane/siloxane mixture was added 0.001 g of ferric chloride. Reaction temperature was maintained at approximately 30° to 35° C.

Samples of the mixture were taken periodically over a period of approximately 44 hours. These samples were analyzed by gas chromatography. Gas chromatographic analyses characterized the samples by the content of Me, $Me_2$, $D_4$, and chloromethylsiloxanes of the formulae,

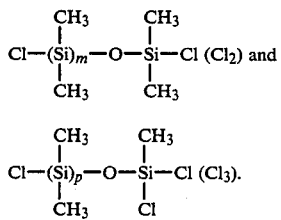

Table 1 is a summary of the analyses of the periodic samples. In Table 1, sample time is expressed in hours and designated "Time"; Me content, $Me_2$ content, $D_4$ content, and content of $Cl_2$ and $Cl_3$ are designated "%Me", "%$Me_2$", "%$D_4$", "%$Cl_2$", and "%$Cl_3$", respectively.

TABLE 1

| Time | % Me | % $Me_2$ | % $D_4$ | % $Cl_2$ | % $Cl_3$ |
|---|---|---|---|---|---|
| 0 | 1.11 | 94.2 | 4.38 | 0.10 | 0 |
| 19 | 1.12 | 94.3 | 2.76 | 0.73 | 0 |
| 24 | 1.11 | 90.8 | 0.69 | 2.47 | 0 |
| 44 | 1.03 | 70.4 | 0 | 26.53 | 0 |

The above results demonstrate that a reaction occurs between dimethyldichlorosilane and octamethylcyclotetrasiloxane in the presence of ferric chloride to produce dichlorodimethylsiloxanes. However, no incorporation of the trifunctional methyltrichlorosilane into siloxane materials has occurred.

EXAMPLE 2

(Not within the scope of the instant invention).

Approximately 100 g of a mixture of $Me_2$, Me, and $D_4$ was added to a reactor as described in Example 1. Reactor temperature was maintained at approximately 30° C. Anhydrous hydrogen chloride gas was bubbled through the mixture.

Samples of the mixture were taken periodically over a period of 43 hours. These samples were analyzed by gas chromatography. Gas chromatographic analyses characterized the samples by the content of Me, $Me_2$, $D_4$, and chloromethylsiloxanes (as defined in Example 1). Table 2 is a summary of the analyses of the periodic samples. The same notation used in Example 1 will be applied to Table 2.

TABLE 2

| Time | % Me | % $Me_2$ | % $D_4$ | % $Cl_2$ | % $Cl_3$ |
|---|---|---|---|---|---|
| 0 | 1.13 | 92.5 | 5.90 | 0.37 | 0 |
| 20 | 1.12 | 92.1 | 6.19 | 0.39 | 0 |
| 24 | 1.10 | 92.0 | 6.34 | 0.46 | 0 |
| 42 | 1.07 | 91.7 | 6.45 | 0.60 | 0 |

The above results demonstrate that hydrogen chloride catalyzes neither the chlorosilane/chlorosiloxane exchange reation nor the reaction of methyltrichlorosilane to form chlorosiloxanes under these conditions.

EXAMPLE 3

Approximately 100 g of a mixture consisting of approximately 1 g Me and 99 g $Me_2$ was added to an agitated laboratory reactor fitted with provisions for heating and venting of gases. To the chlorosilane mixture was added of 0.8 g water. To the agitated mixture was then added 0.6 g of 85 percent o-phosphoric acid. The reaction mixture was maintained at approximately 30° C. at atmospheric pressure.

Samples of the reaction mixture were taken periodically over a period of 116 hours. These samples were analyzed by gas chromatography. Gas chromatographic analyses characterized the samples by the content of Me, $Me_2$, $D_4$, and chloromethylsiloxanes (as defined in Example 1). Table 3 is a summary of the analyses of the periodic samples. The same notation used in Example 1 will be applied to Table 3.

TABLE 3

| Time | % Me | % $Me_2$ | % $D_4$ | % $Cl_2$ | % $Cl_3$ |
|---|---|---|---|---|---|
| 0 | 1.16 | 92.8 | 0.1 | 5.17 | 0 |
| 1 | 0.76 | 90.3 | <0.1 | 8.32 | 0.31 |

TABLE 3-continued

| Time | % Me | % Me₂ | % D₄ | % Cl₂ | % Cl₃ |
|---|---|---|---|---|---|
| 3 | 0.46 | 89.9 | <0.1 | 8.83 | 0.55 |
| 19.5 | 0.21 | 89.7 | <0.1 | 9.08 | 0.69 |
| 24.8 | 0.17 | 89.3 | <0.1 | 9.12 | 0.71 |
| 94.5 | 0.04 | 90.2 | <0.1 | 8.62 | 0.52 |
| 116 | 0.03 | 89.7 | 0 | 9.00 | 0.54 |

The reactor contents were then distilled to a reactor temperature of approximately 100° C. The distillate recovered was analyzed by gas chromatography and found to be Me₂ with less than 400 ppm Me.

The above results demonstrate that an equilibrium is established between dimethyldichlorosilane and dichlorosiloxane species. The results further indicate that methyltrichlorosilane is consumed, and that this disappearance of methyltrichlorosilane corresponds to an increase in the trichlorosiloxane species. More significantly, the above results demonstrate that the treatment of the dimethyldichlorosilane/methyltrichlorosilane mixture, as described above, yields dimethyldichlorosilane with a significantly reduced level of methyltrichlorosilane.

EXAMPLE 4

Approximately 4 g of polydimethylsiloxanediol,

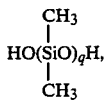

was added to 109 g of a mixture consisting of approximately 1 percent Me in Me₂ in a laboratory reactor as described in the above examples. The polydimethylsiloxanediol had a g of approximately 50. To this mixture was added 0.8 g 85 percent o-phosphoric acid. The reactor was fitted with provisions to maintain a hydrogen chloride pressure of approximately 5 pounds per square inch, gauge (psig). The mixture was held at approximately 45° C.

Samples of the mixture were taken periodically over a period of 115 hours. These samples were analyzed by gas chromatography. Gas chromatographic analyses characterized the samples by the content of Me, Me₂, D₄, and chloromethylsiloxanes (as defined in Example 1). Table 4 is a summary of the analyses of the periodic samples. The same notation used in Example 1 will be applied to Table 4.

TABLE 4

| Time | % Me | % Me₂ | % D₄ | % Cl₂ | % Cl₃ |
|---|---|---|---|---|---|
| 0 | 1.17 | 98.7 | <0.01 | 0.03 | 0 |
| 17.5 | 1.06 | 95.1 | 0.05 | 0.03 | 0 |
| 19.8 | 0.28 | 88.7 | 0.02 | 4.34 | 0.52 |
| 43 | 0.05 | 85.9 | <0.01 | 7.79 | 0.66 |
| 115 | 0.04 | 85.1 | 0.01 | 7.92 | 0.81 |

The above results demonstrate that polydimethylsiloxanediols are a suitable source of siloxane materials for the desired chlorosilane/siloxane exchange. The above results demonstrate that an equilibrium is established between dimethyldichlorosilane and dichlorosiloxane species. The results further indicate that methyltrichlorosilane is consumed, and that this disappearance of methyltrichlorosilane corresponds to an increase in the trichlorosiloxanes species.

EXAMPLE 5

A 105 g mixture of Me₂/Me/D₄ was added to a vessel as described in Example 3. To this mixture was added approximately 9 g of Duolite ES-467 ion exchange resin. This weak-acid type resin has an amino-phosphonic functionality bonded to a polystyrene polymer. Duolit ES-467 is a brand name of Diamond Shamrock Corporation, Cleveland, Ohio. Evolution of gas, assumed to be hydrogen chloride was noticeable. The reactor pressure was maintained at 5 psig and the temperature was held at 48° C.

Samples of the mixture were taken periodically over a period of 50 hours. These samples were analyzed by gas chromatography. Gas chromatographic analyses characterized the samples by the content of Me, Me₂, D₄, and chloromethylsiloxanes (as defined in Example 1). Table 5 is a summary of the analyses of the periodic samples. The same notation used in Example 1 will be applied to Table 5.

TABLE 5

| Time | % Me | % Me₂ | % D₄ | % Cl₂ | % Cl₃ |
|---|---|---|---|---|---|
| 0 | 1.15 | 91.0 | 7.71 | 0.03 | 0 |
| 2.5 | 0.28 | 85.4 | 6.89 | 4.10 | 0.70 |
| 5.5 | 0.11 | 84.3 | 5.33 | 5.36 | 0.87 |
| 24 | 0.021 | 79.6 | 0.97 | 10.60 | 1.04 |
| 28.8 | 0.017 | 78.6 | 0.54 | 14.07 | 1.05 |
| 50 | 0.015 | 76.3 | 0.12 | 17.74 | 1.13 |

These above results further demonstrate that phosphorous-containing materials promote the consumption of methyltrichlorosilane with incorporation into the trichlorosiloxane materials.

EXAMPLE 6

75 g of a Me/Me₂/D₄ mixture was charged to a reactor, as described in Example 4. To this mixture was added 10 g of silica gel. The silica gel had an average particle size of 70 microns. The mixture of solid and liquid was agitated throughout. Temperature of the slurry was maintained at about 45° C.; and pressure was maintained at 5 psig.

Samples were taken after approximately 75 hours. The samples were analyzed by gas chromatography. The analyses showed essentially no consumption of the Me.

At this point, 0.5 g of 85 percent o-phosphoric acid was added to the mixture. A sample was taken after 90 minutes. This sample is designated as Sample A. Gas chromatography showed that the sample had less than 0.001 percent Me. An additional 1.2 g Me was added to the reaction mixture. The mixture was subsequently sampled over a period of 47 hours. This mixture is designated Sample B. These samples were analyzed by gas chromatography. Gas chromatographic analyses characterized the samples by the content of Me, Me₂, D₄, and chloromethylsiloxanes (as defined in Example 1). Table 6 is a summary of the analyses of the periodic samples. The same notation used in Example 1 will be applied to Table 6.

TABLE 6

| Sample | Time | % Me | % Me₂ | % D₄ | % Cl₂ | % Cl₃ |
|---|---|---|---|---|---|---|
| A | 0 | 1.11 | 88.3 | 6.23 | 2.48 | <0.01 |
| | 1.5 | 0.005 | 77.2 | 0 | 21.21 | 0.46 |
| | 20 | 0.005 | 73.73 | 0 | 25.10 | 0.65 |
| B | 0 | 1.38 | 71.73 | 0 | 25.57 | 0.82 |
| | 4.2 | 0.38 | 73.57 | 0 | 23.57 | 1.91 |

TABLE 6-continued

| Sample | Time | % Me | % Me$_2$ | % D$_4$ | % Cl$_2$ | % Cl$_3$ |
|---|---|---|---|---|---|---|
| | 23.2 | 0.018 | 75.00 | 0 | 22.54 | 1.63 |
| | 47 | 0.011 | 74.82 | 0 | 22.48 | 1.87 |

These above results demonstrate that phosphorous materials promote the conversion of methyltrichlorosilane into trichlorosiloxane materials.

EXAMPLE 7

Approximately 100 g of a Me/Me$_2$/D$_4$ mixture was added to a reactor similar to that used in Example 4. The mixture was heated to and held at 41° C. 15 g of activated carbon was added to the reaction mixture. The activated carbon was Darco Grade 4×12, produced by Atlas Chemical Industries. Gaseous hydrogen chloride was noted being generated from the reaction of water in the activated carbon and the chlorosilanes. The pressure of the reactor was maintained at 10 psig.

Samples of the mixture were taken periodically over a period of 122 hours. These samples were analyzed by gas chromatography. Gas chromatographic analyses characterized the samples by the content of Me, Me$_2$, D$_4$, and chloromethylsiloxanes (as defined in Example 1). Table 7 is a summary of the analyses of the periodic samples. The same notation used in Example 1 will be applied to Table 7.

TABLE 7

| Time | % Me | % Me$_2$ | % D$_4$ | % Cl$_2$ | % Cl$_3$ |
|---|---|---|---|---|---|
| 0 | 1.43 | 89.14 | 9.25 | 0.01 | 0 |
| 4.2 | 0.56 | 71.28 | 0.011 | 25.32 | 0.93 |
| 23.5 | 0.18 | 64.59 | 0.016 | 33.06 | 1.50 |
| 28.8 | 0.14 | 64.49 | n.a. | 32.93 | 1.52 |
| 122.5 | 0.009 | 63.93 | n.a. | 33.53 | 1.62 |

The above results demonstrate that activated carbon in the presence of hydrogen chloride is an effective catalyst for the reaction of methyltrichlorosilane to form trichlorosiloxanes.

EXAMPLE 8

Another run was made using the apparatus and procedures of Example 7. The only change was to hold the temperature at 67° C.

Samples of the mixture were taken periodically over a period of 120 hours. These samples were analyzed by gas chromatography. Gas chromatographic analyses characterized the samples by the content of Me, Me$_2$, D$_4$, and chloromethylsiloxanes (as defined in Example 1). Table 8 is a summary of the analyses of the periodic samples. The same notation used in Example 1 will be applied to Table 8.

TABLE 8

| Time | % Me | % Me$_2$ | % D$_4$ | % Cl$_2$ | % Cl$_3$ |
|---|---|---|---|---|---|
| 0 | 1.96 | 88.28 | 9.64 | 0.03 | 0 |
| 2.2 | 0.86 | 87.48 | 6.83 | 1.17 | 0.56 |
| 22 | 0.054 | 83.72 | 0.04 | 8.34 | 0.93 |
| 45 | 0.030 | 81.60 | n.a. | 12.37 | 1.10 |
| 119.5 | 0.011 | 72.78 | n.a. | 21.90 | 1.93 |

The above results further demonstrate that activated carbon is an effective catalyst for the conversion of methyltrichlorosilane to trichlorosiloxanes. The results also indicate that temperature does not significantly effect the course of this reaction.

EXAMPLE 9

Approximately 100 g of a Me/Me$_2$/D$_4$ mixture was added to the apparatus described in the previous examples. This mixture was heated to and maintained at a temperature of 46° C. To the agitated mixture was add 4 g of Amberlyst A-26 ion exchange resin beads. Amberlyst A-26 is a commercially available material purchased from Rohm and Haas. Amberlyst A-26 is a strong base type resin having amino-functional groups bonded to a polymer backbone. The resin has a moisture content of 50 weight percent. Evolution of hydrogen chloride gas was evident upon addition of the resin to the mixture.

Samples of the mixture were taken periodically over a period of 36 hours. These samples were analyzed by gas chromatography. Gas chromatographic analyses characterized the samples by the content of Me, Me$_2$, D$_4$, and chloromethylsiloxanes (as defined in Example 1). Table 9 is a summary of the analyses of the periodic samples. The same notation used in Example 1 will be applied to Table 9.

TABLE 9

| Time | % Me | % Me$_2$ | % D$_4$ | % Cl$_2$ | % Cl$_3$ |
|---|---|---|---|---|---|
| 0 | 1.16 | 91.38 | 7.26 | 0.01 | 0 |
| 2.8 | 0.32 | 83.11 | 2.42 | 11.35 | 1.02 |
| 35.8 | 0.15 | 80.45 | 0.08 | 15.89 | 1.27 |

The above results demonstrate that a nitrogen-containing material can be utilized as a catalyst for the conversion of methyltrichlorosilane to a trichlorosiloxane.

EXAMPLE 10

The use of N,N-dimethylformamide was evaluated as a catalyst. Apparatus and procedures utilized in the previous examples were employed. A 100 g Me/Me$_2$/D$_4$ mixture was added to the reactor. Approximately 7 g of dimethylformamide was added to the agitated mixture.

Samples of the mixture were taken periodically over a period of 36 hours. These samples were analyzed by gas chromatography. Gas chromatographic analyses characterized the samples by the content of Me, Me$_2$, octamethylcyclosiloxane (D$_4$), and chloromethylsiloxanes (as defined in Example 1). Table 10 is a summary of the analyses of the periodic samples. The same notation used in Example 1 will be applied to Table 10.

TABLE 10

| Time | % Me | % Me$_2$ | % D$_4$ | % Cl$_2$ | % Cl$_3$ |
|---|---|---|---|---|---|
| 0 | 1.16 | 91.21 | 7.48 | 0.02 | 0 |
| 3 | 1.09 | 90.86 | 6.73 | 0.41 | 0.03 |
| 30.2 | 0.77 | 80.93 | 0.30 | 2.27 | 0.12 |

The gas chromatographic analyses also show a significant amount of higher boiling materials, believed to be higher siloxane materials.

The above results demonstrate that N,N-dimethylformamide can be a catalyst for the conversion of methyltrichlorosilane to higher-boiling siloxanes.

EXAMPLE 11

A series of seven runs was made to study the effects of catalyst concentration and siloxane concentration upon the conversion of methyltrichlorosilane to trichlorosiloxanes. The apparatus and procedures utilized were similar to those described in the previous examples. A modification was made to the procedure in the fact that the Me$_2$, the D$_4$, and the o-phosphoric acid were allowed to mix together overnight in the reactor to facilitate formation of the dichlorosiloxane species. The four runs are identified as Samples D, E, F, G, H, J and K, respectively. All runs were made at a temperature of approximately 30° C. and a pressure of approximately 3 psig. Table 11 summarizes the conditions under which the runs were made. The conditions identified are the weight percent Me in the sample, designated as "%Me"; the weight percent D$_4$, designated "%D$_4$"; and the weight percent o-phosphoric acid, designated as "%Cat"; the remainder of the sample being Me$_2$.

TABLE 11

| Sample | % Me | % D$_4$ | % Cat |
|---|---|---|---|
| D | 1.0 | 11.0 | 0.5 |
| E | 1.0 | 11.0 | 5.0 |
| F | 0.55 | 2.0 | 0.5 |
| G | 0.55 | 2.0 | 5.0 |
| H | 0.55 | 20.0 | 0.5 |
| J | 1.0 | 2.0 | 2.75 |
| K | 1.0 | 20.0 | 2.75 |

It was found that at the higher levels of catalyst and D$_4$ concentrations, reaction occurred very rapidly. To facilitate sample analyses, gas samples from the vapor space in the reactor were taken to separate the Me and Me$_2$ materials from the catalyst in the reactor to avoid further reaction of the samples before they could be analyzed. The reactor was sampled at 15, 30, and 60 minutes, 2, and 4 hours, respectively. The chlorosilane samples taken after 4 hours were distilled from the reactor until the temperature of the reactor contents reached 120° C.

Table 12 is a summary of these runs. The results for the reaction samples at various times, designated by the time in minutes ("min") or hours ("hr"); and the distillate, designated as "Dist" samples are reported in ppm Me in Me$_2$.

TABLE 12

| Sample | 15 min | 30 min | 60 min | 2 hr | 4 hr | Dist |
|---|---|---|---|---|---|---|
| D | 5730 | 6070 | 5690 | 5220 | 3850 | 3490 |
| E | <100 | <100 | <100 | <100 | <100 | <100 |
| F | 5640 | 6650 | 6570 | 7220 | 5870 | 5330 |
| G | 270 | <100 | <100 | <100 | <100 | <100 |
| H | 7650 | 5790 | 7540 | 3700 | 3990 | 4850 |
| J | 385 | 1490 | <100 | 130 | | 170 |
| K | <100 | <100 | <100 | <100 | <100 | <100 |

The above results demonstrate that the concentration of catalyst and concentration of D$_4$ (or other siloxanes) significantly affect the rate at which methyltrichlorosilane is consumed as higher boiling trichlorosiloxanes.

EXAMPLE 12

A laboratory apparatus was assembled to evaluate the continuous treatment of dimethyldichlorosilane with siloxanes and activated carbon to reduce the methyltrichlorosilane content of the dimethyldichlorosilane.

The laboratory apparatus consisted of a 1-liter three-neck flask with a glass column fitted to the middle neck. The column was ¾ inches in diameter and approximately 8 inches long. The column was filled with approximately 35 ml of activated carbon granules. The activated carbon was Calgon PCB, 12×30 mesh. The flask was placed in a hemispherical heating mantle, and the column was wrapped with electrical heating tape. The electrical input to the heating mantel and the heating tape was controlled to maintain a controlled temperature in the flask and in the column.

A liquid feed mixture of dimethyldichlorosilane and methyltrichlorosilane was fed to the flask with a laboratory syringe pump. Hydrogen chloride gas was fed to the flask from a compressed gas cylinder. Gas flow was controlled with a rotameter. The dimethyldichlorosilane/methyltrichlorosilane mixture was vaporized in the flask. A liquid feed of chlorine-endblocked dimethylsiloxanes was fed to the top of the column with a laboratory syringe pump. In operation of the apparatus, the chlorosilane vapors and hydrogen chloride gas passed upward into the column. These vapors contacted the liquid siloxane passing downward in to column. The column temperature was controlled at about 130° C. to facilitate passage of vapors of treated dimethyldichlorosilane to pass out of the column. These vapors were condensed and analyzed by gas chromatography. The siloxanes were collected in the flask.

Dimethyldichlorosilane containing 1.08 weight percent methyltrichlorosilane was fed to the flask at a rate of 16 ml/hr. Hydrogen chloride gas was fed at 0.5 l/hr. The siloxane was fed to the top of the column at approximately 16 ml/hr. The dimethyldichlorosilane collected off the top of the column contained less than 100 ppm methyltrichlorosilane.

The above results demonstrate that the methyltrichlorosilane content of dimethyldichlorosilane can be significantly reduced by treatment with a chlorosiloxane material in the presence of activated carbon in a continuous mode.

EXAMPLE 13

A laboratory apparatus was assembled to evaluate the continuous treatment of dimethyldichlorosilane with siloxanes and a phosphorous-containing material to reduce the methyltrichlorosilane content of the dimethyldichloro- silane.

The equipment and procedures utilized were similar to those used in Example 12. The column, rather than a packed column, was a ten-tray bubble-cap column. The bubble-cap tray section was about 2 cm in diameter and 25 cm tall. The bubble-cap column was housed in a vacuum jacket. Additionally, the dimethyldichlorosilane feed was passed through a preheater before being fed to the flask.

The dimethyldichlorosilane feed contained 0.5 weight percent methyltrichlorosilane. A siloxane/-catalyst feed was prepared by mixing 60 g dimethyldichlorosilane with 35 g of octamethylcyclotetrasiloxane; to this mixture was slowly added 5 gm of reagent grade 85 percent ortho-phosphoric acid.

The preheater temperature was maintained at 110° C. The flask temperature was controlled at 120° C. The top of the column was controlled at 85° C.

An extended run of 160 hours was made. The dimethyldichlorosilane was fed at a rate of from about 0.6 to 0.9 g/hr. Hydrogen chloride gas was fed at a rate of 0.7 g/hr. The siloxane/catalyst mixture was fed to the top of the column at a rate of from about 0.01 to 0.04 ml/hr.

Samples of the treated dimethyldichlorosilane taken during the course of the run had methyltrichlorosilane content of less than 100 ppm on a weight basis.

The above results demonstrate that the methyltrichlorosilane content of dimethyldichlorosilane can be significantly reduced by treatment with siloxane material in the presence of a phosphorous-containing catalyst in a continuous mode.

EXAMPLE 14

About 600 g crude diphenyldichlorosilane (Ph$_2$), (C$_6$H$_5$)$_2$SiCl$_2$, and about 60 g octaphenylcyclotetrasiloxane (Ph$_2$ Cyclics), were added to a 1-liter flask. The flask was fitted with a mechanical agitator, provisions for heating and cooling, provisions for the addition of liquid and vapor feeds, and provisions for venting gases. The flask was purged with nitrogen. About 30 g o-phosphoric acid (85% industrial grade) was slowly added to the flask over a period of 10 to 15 minutes with vapors, thought to be hydrogen chloride (HCl), venting from the system. The flask and its contents were heated to 55° C. HCl gas was bubbled through the mixture in the flask from a compressed gas cylinder.

The flask and its contents were held at these conditions for approximately two days. The contents of the flask were sampled at 1.25 and 10 hours after the system had reached 50° C. These samples were analyzed by a gas chromatographic (GC) technique. The individual chemical species had been previously identified by a gas chromatographic/mass spectographic technique.

The crude Ph$_2$ had as the major impurities, trifunctional chlorosilane materials of the general formula, $$R^{ii}SiCl_3,$$

wherein $R^{ii}$ is substituted alkyl or substituted aryl groups. Some of the trifunctional chlorosilanes identified in the crude Ph$_2$ are: Cl$_3$SiC$_6$H$_{10}$SiCl$_3$, Cl$_2$C$_6$H$_5$SiCH$_2$SiCl$_3$, (SiCl$_3$)$_2$C$_6$H$_3$SiCl$_3$, (SiCl$_3$OSiCl$_2$)C$_6$H$_4$SiCl$_3$, C$_6$H$_5$SiCl$_2$CH(CH$_3$)SiCl$_3$, C$_5$H$_{11}$C$_6$H$_4$SiCl$_3$, Cl$_3$SiC$_6$H$_4$CH$_2$SiCl$_3$, and C$_3$H$_7$SiCl$_2$C$_6$H$_4$SiCl$_3$.

Table 13 is a summary of the analyses of the mixture taken before reaction and after 1.25 and 10 hours, respectively, after the mixture had been brought to temperature. In Table 13, the samples are designated by the time in hours at which they were taken, designated as "Time"; the results of the analysis are reported in the GC area percent, based upon the chlorosilanes present, designated as "Percent". The chlorosilanes are designated as "Component". The components identified are the desired Ph$_2$ and the total trifunctional chlorosilane content; designated as "Ph$_2$" and "Trichlor", respectively.

TABLE 13

| Time | Percent | | |
|---|---|---|---|
| | 0 | 1.25 | 10.0 |
| Component | | | |
| Ph$_2$ | 88.1 | 97.7 | 97.8 |
| Trichlor | 5.1 | 0.7 | 0.5 |

The above results demonstrate that the trifunctional chlorosilane content of a crude diphenyldichlorosilane mixture can be reduced by reaction with a phenylsiloxane in the presence of phosphoric acid.

EXAMPLE 15

A second run was carried out using the apparatus and procedures of Example 14. Ph$_2$ purified by this procedure was isolated by distillation.

614.8 g of crude Ph$_2$, 61.4 g of Ph$_2$ Cyclics, and 31.1 g of phosphoric acid were utilized. The contents of the flask were sampled at the start of the run and 1.1 and 9 hours after the flask and its contents reached 50° C.

Table 14 is a summary of the results. The notation used is Example 14 is applied.

TABLE 14

| Time | Percent | | |
|---|---|---|---|
| | 0 | 1.1 | 10.0 |
| Component | | | |
| Ph$_2$ | 89.2 | 97.3 | 97.7 |
| Trichlor | 4.7 | 0.8 | 0.7 |

The contents of the flask were then distilled in a standard batch, vacuum distillation. Pressure was maintained at 11 mm Hg at a flask temperature of about 160° to 170° C. A reflux ratio of 10/1 was utilized. The Ph$_2$ recovered had a trifunctional content of 1 percent of less.

The above results demonstrate that the trifunctional chlorosilane content of a crude diphenyldichlorosilane mixture can be reduced by reaction with a phenylsiloxane in the presence of phosphoric acid. Further, the above results demonstrate that diphenyldichlorosilane, so purified, can be recovered by distillation.

What is claimed is:

1. A process for the purification of an organosilane, having the formula, $$R^i_a SiX_{4-a},$$

wherein each $R^i$ is independently selected from a group consisting of hydrogen atoms, alkyl groups. substituted alkyl groups, alkenyl groups, and aryl groups; wherein each X is an independently selected halogen atom; wherein a has a value of 1, 2, 3, or 4; and wherein at least one $R^i$ must be an alkyl group, a substituted alkyl group, an alkenyl group, or an aryl group, wherein the content of more highly functional silanes having the formula, $$R^{ii}_b SiX_{4-b},$$

wherein each $R^{ii}$ is independently selected from a group consisting of alkyl groups, substituted alkyl groups, alkenyl groups, aryl groups, and substituted aryl groups, wherein b has a value of 0, 1, 2, or 3 and wherein b must be less than a; and wherein X is defined above, is reduced, said process comprising (A) contacting a mixture comprising a major portion of the organosilane and a minor portion of one or more more highly functional silanes, with organosiloxanes, and a sufficient quantity of a catalyst effective in promoting reaction between said more highly functional silanes and said organosiloxanes, wherein the organosiloxanes are selected from a group consisting of

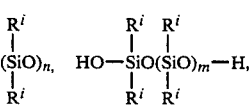

-continued

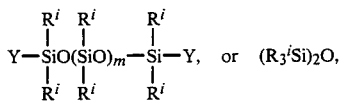  5 wherein $R^i$ is defined above; wherein each Y is independently selected from a group consisting of halogen atoms and trialkylsiloxy groups; wherein n has a value of 3 to 9, inclusive; and wherein m has a value of less than about 1000;

(B) facilitating the reaction between the more highly functional silanes and the organosiloxane to convert the more highly functional silanes to polyfunctional siloxanes, said polyfunctional siloxanes having the formula,

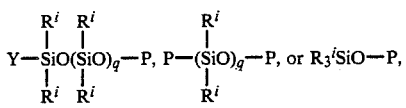  20 wherein each P is independently selected from a group consisting of $-SiR^{ii}_2X$, $-SiR^{ii}X_2$, and $-SiX_3$ radicals, wherein each $R^{ii}$, X, and Y are independently selected and are defined above; and wherein q has a value of less than about 1000; and (C) isolating the organosilane from the polyfunctional siloxanes and the organosiloxanes.

2. A process for the purification of an organosilane, having the formula, $R^i_c SiX_{4-c}$, wherein each $R^i$ is independently selected from a group consisting of hydrogen atoms, alkyl groups, substituted alkyl groups, alkenyl groups, and aryl groups; wherein each X is an independently selected halogen atom; wherein c has a value of 2, 3, or 4; and wherein at least one $R^i$ must be an alkyl group, a substituted alkyl group, an alkenyl group, or an aryl group, wherein the content of more highly functional silanes having the formula, $R^{ii}_d SiX_{4-d}$, wherein each $R^{ii}$ is independently selected from a group consisting of alkyl groups, substituted alkyl groups, alkenyl groups, aryl groups, and substituted aryl groups; wherein X is as defined above; and wherein d has a value of 0 or 1, is reduced, said process comprising (A) contacting a mixture comprising a major portion of the organosilane and a minor portion of one or more more highly functional silanes with organosiloxanes, and a sufficient quantity of a catalyst effective in promoting reaction between said more highly functional silanes and said organosiloxanes, wherein the organosiloxanes are selected from a group consisting of

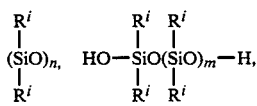

-continued

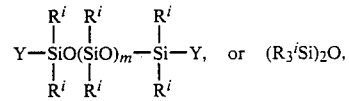

wherein $R^i$ is defined above; wherein each Y is independently selected from a group consisting of halogen atoms and trialkylsiloxy groups; wherein n has a value of 3 to 9, inclusive; and wherein m has a value of less than about 1000;

(B) facilitating the reaction between the more highly functional silanes and the organosiloxane to convert the more highly functional silanes to polyfunctional siloxanes, said polyfunctional siloxanes having the formula,

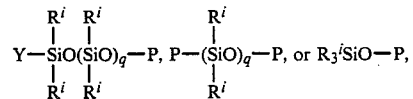

wherein each P is independently selected from a group consisting of $-SiR^{ii}X_2$, and $-SiX_3$ radicals. wherein each $R^{ii}$, X, and Y are independently selected and are defined above; and wherein q has a value of less than about 1000; and (C) isolating the organosilane from the polyfunctional siloxanes and the organosiloxanes.

3. A process according to claim 1, wherein the catalyst is selected from a group consisting of phosphorous-containing compounds, nitrogen-containing compounds, and activated carbon.

4. A process according to claim 2, wherein the catalyst is selected from a group consisting of phosphorous-containing compounds, nitrogen-containing compounds, and activated carbon.

5. A process according to claim 1, wherein the process further comprises contacting a hydrogen halide with said mixture of organosilane and more highly functional silanes, said organosiloxanes, and said catalyst.

6. A process according to claim 2, wherein the process further comprises contacting a hydrogen halide with said mixture of organosilane and more highly functional silanes, said organosiloxanes, and said catalyst.

7. A process according to claim 2, wherein said more highly functional silanes are present in the mixture at a concentration less than about 5.0 weight percent.

8. A process according to claim 2, wherein the mixture is contacted with greater than about 1 weight percent of organosiloxanes relative to the weight of the mixture.

9. A process according to claim 4, wherein the catalyst is a phosphorous-containing compound.

10. A process according to claim 9, wherein the phosphorous-containing compound is selected from a group consisting of phosphoric acids, organophosphoric acids, organophosphonates, phosphonitrile halides, quaternary phosphonium halides, and phosphine oxides.

11. A process according to claim 9, wherein the phosphorous-containing compound is on a solid support.

12. A process according to claim 9, wherein the mixture is contacted with greater than about 0.1 weight percent of the phosphorous-containing material relative to the weight of the mixture.

13. A process according to claim 4, wherein the catalyst is a nitrogen-containing compound.

14. A process according to claim 13, wherein the nitrogen-containing compounds are selected from a group consisting of aliphatic amines, aromatic amines, quaternary ammonium hydroxides, quaternary ammonium halides, amine hydrohalides, carboxylic acid salts of amines, and carboxylic acid salts of quaternary ammonium hydroxides.

15. A process according to claim 4, wherein the catalyst is activated carbon.

16. A process according to claim 15, wherein the mixture is contacted with greater than about 2 weight percent of activated carbon relative to the weight of the mixture.

17. A process according to claim 2, wherein the reaction is facilitated at a temperature greater than about 20° C.

18. A process according to claim 2, wherein isolating the organosilane from the polyfunctional siloxanes and the organosiloxanes is effected by distillation.

19. A process according to claim 2, wherein the process is carried out in a batch mode.

20. A process according to claim 2, wherein the process is carried out in a continuous mode.

21. A process according to claim 2, wherein the organosilane is dimethyldichlorosilane, the more highly functional silane is methyltrichlorosilane, the organosiloxane is selected from a group consisting of

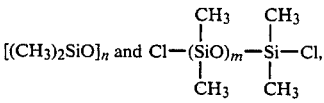

the catalyst is phosphoric acid; wherein the mixture comprises greater than about 0.1 weight percent methyltrichlorosilane; wherein the mixture is contacted with greater about 1 weight percent of organosiloxanes relative to the weight of the mixture; wherein the concentration of the phosphoric acid is in a range of about 0.1 to 5 weight percent relative to the weight of the mixture; wherein reaction is facilitated at a temperature greater than about 20° C.; and wherein the dimethyldichlorosilane is isolated by distillation, the methyltrichlorosilane content of the isolated dimethyldichlorosilane being reduced by greater than about 90 percent.

22. A process according to claim 2, wherein the organosilane is diphenyldichlorosilane; wherein the more highly functional silanes have the formula, $R^{ii}SiX_3$, the organosiloxane is $[(C_6H_5)_2SiO]_n$, the catalyst is phosphoric acid; wherein the mixture comprises greater than about 1 weight percent $R^{ii}SiX_3$; wherein the mixture is contacted with greater about 1 weight percent of organosiloxanes relative to the weight of the mixture; wherein the concentration of the phosphoric acid is in a range of about 1 to 10 weight percent relative to the weight of the mixture; wherein reaction is facilitated at a temperature greater than about 20° C.; and wherein the diphenyldichlorosilane is isolated by distillation, the more highly functional silane content of the isolated diphenyldichlorosilane being reduced by greater than about 80 percent.

* * * * *